(12) United States Patent
Kang et al.

(10) Patent No.: US 7,544,633 B2
(45) Date of Patent: *Jun. 9, 2009

(54) CATALYST FOR PARTIAL OXIDATION AND PREPARATION METHOD THEREOF

(75) Inventors: Jung-Hwa Kang, Seoul (KR); Won-Ho Lee, Daejeon (KR); Min-Ho Kil, Daejeon (KR); Sang-Heup Moon, Seoul (KR); Bu-Young Jo, Seoul (KR)

(73) Assignee: LG Chem, Ltd., Seoul (KR)

( * ) Notice: Subject to any disclaimer, the term of this patent is extended or adjusted under 35 U.S.C. 154(b) by 625 days.

This patent is subject to a terminal disclaimer.

(21) Appl. No.: 11/064,016

(22) Filed: Feb. 24, 2005

(65) Prior Publication Data

US 2005/0187406 A1     Aug. 25, 2005

(30) Foreign Application Priority Data

Feb. 25, 2004   (KR) .................. 10-2004-0012646

(51) Int. Cl.
  *B01J 23/24*     (2006.01)
  *B01J 23/28*     (2006.01)
  *B01J 23/74*     (2006.01)
  *B01J 23/882*    (2006.01)
  *B01J 23/883*    (2006.01)

(52) U.S. Cl. .............. 502/311; 502/313; 502/314; 502/315; 502/316; 502/321

(58) Field of Classification Search .......... 502/311, 502/313, 314, 315, 316, 321, 255
See application file for complete search history.

(56) References Cited

U.S. PATENT DOCUMENTS

| 2,941,007 | A | 6/1960 | Callahan et al. |
| 3,089,909 | A | 5/1963 | Barclay et al. |
| 3,171,859 | A | 3/1965 | Sennewald et al. |
| 3,522,299 | A | 7/1970 | Takenaka et al. |
| 3,825,600 | A | 7/1974 | Ohara et al. |
| 4,224,187 | A | 9/1980 | Vanderspurt |
| 4,248,803 | A | 2/1981 | Vanderspurt |
| 4,873,217 | A | 10/1989 | Kawajiri et al. |
| 5,017,542 | A | 5/1991 | Martan et al. |
| 5,602,280 | A | 2/1997 | Nagai et al. |
| 5,658,842 | A | 8/1997 | Midorikawa et al. |
| 7,005,403 | B2 * | 2/2006 | Borgmeier et al. .......... 502/312 |
| 7,341,974 | B2 * | 3/2008 | Kang et al. ................. 502/311 |

FOREIGN PATENT DOCUMENTS

| CN | 1210511 A | 3/1999 |
| DE | 27 29 841 | 1/1979 |
| EP | 0 501 794 | 2/1992 |
| EP | 0 523 727 | 1/1993 |
| JP | 52-083306 | 7/1977 |
| JP | 02-025443 | 1/1990 |
| JP | 05-023596 | 2/1993 |
| JP | 08-040969 | 2/1996 |
| JP | 10-216523 | 8/1998 |
| JP | 2002-097164 | 4/2002 |
| KR | 10-2002-0027023 | 4/2002 |
| KR | 10-2002-0043801 | 6/2002 |
| KR | 10-2003-0018917 | 3/2003 |

* cited by examiner

*Primary Examiner*—James O Wilson
*Assistant Examiner*—Ebenezer Sackey
(74) *Attorney, Agent, or Firm*—McKenna Long & Aldridge, LLP

(57) ABSTRACT

The present invention relates to a catalyst for partial oxidation and a preparation method thereof, more particularly to a preparation method of a complex metal oxide catalyst that shows high activity for conversion of propylene or isobutylene, maintains good selectivity for such unsaturated aldehyde as acrolein or methacrolein and improves production yield of such unsaturated carboxylic acid as acrylic acid or methacrylic acid through stable process by using a drying control chemical additive.

9 Claims, No Drawings

CATALYST FOR PARTIAL OXIDATION AND PREPARATION METHOD THEREOF

CROSS-REFERENCE TO RELATED APPLICATION

This application claims priority of Korean Patent Application No. 10-2004-0012646 filed on Feb. 25, 2004 in the Korean Intellectual Property Office, the entire disclosure of which is incorporated herein by reference.

TECHNICAL FIELD

The present invention relates to a catalyst for partial oxidation and a preparation method thereof, more particularly to a complex metal oxide catalyst useful in the process of manufacturing such unsaturated aldehyde as acrolein or methacrolein by reacting a gas containing air or oxygen with propylene or isobutylene and a preparation method thereof.

BACKGROUND ART

Acrylic acid is the base material of a variety of acrylates widely used for highly-absorbent resins and paints, adhesives, polishes, electrical insulating materials and processing of leather, fiber, paper, etc. With the development in polymer processing techniques, demand on acrylic acid is increasing consistently.

Acrylic acid or methacrylic acid is industrially manufactured by partially oxidizing propylene or isobutylene and then oxidizing acrolein or methacrolein, which are obtained from the partial oxidation.

That is to say, the process of manufacturing acrylic acid or methacrylic acid from partial oxidation of propylene or isobutylene comprises two reaction steps. In the first step, propylene or isobutylene is oxidized to acrolein or methacrolein using an oxide catalyst comprising molybdenum and bismuth as key constituent. In the second step, acrolein or methacrolein is oxidized again to acrylic acid or methacrylic acid using an oxide catalyst comprising molybdenum and vanadium.

In the manufacture of acrylic acid or methacrylic acid, selectivity improves with the performance of the catalyst. Hence, researches for improving performance of the Mo—Bi catalyst are being performed actively.

U.S. Pat. No. 2,941,007 (J. L. Callahan, et al.) disclosed a catalyst comprising bismuth molybdate or bismuth phosphomolybdate. U.S. Pat. No. 3,171,859 (K. Sennewald, et al.) disclosed a catalyst comprising Fe, Bi, P, Mo and O. U.S. Pat. No. 3,522,299 (S. Takenaka, et al.) disclosed a catalyst comprising Ni, Co, Fe, Bi, Mo, P, As and O. U.S. Pat. No. 3,089,909 (J. L. Barclay, et al.) disclosed a catalyst comprising a compound selected from the group consisting of tin tungstate, tungstic acid and bismuth tungstate. U.S. Pat. No. 3,825,600 (T. Ohara, et al.) disclosed a catalyst comprising Mo, Co, Fe, Bi, W, Si and an alkali metal. Korean Laid-Open Patent Publication No. 2003-18917, Korean Laid-Open Patent Publication No. 2002-43801, U.S. Pat. No. 4,873,217 and U.S. Pat. No. 4,224,187 disclosed methods of improving catalytic performance by a variety of preparing methods. U.S. Pat. No. 4,248,803 and U.S. Pat. No. 5,017,542 proposed a catalyst having an improved propylene conversion ratio and offering good acrolein and acrylic acid yields by controlling the composition and content of the catalyst. However, with these methods, it is difficult to keep the suspension of the catalyst for partial oxidation of propylene or isobutylene to acrolein or methacrolein uniform because anionic metal salts and cationic metal salts present in the aqueous solution react with each other and the resultant precipitates sediment quickly. Resultantly, the precipitate is separated from the water layer.

To solve this problem, Korean Laid-Open Patent Publication No. 2002-27023 disclosed a method of preparing a uniform suspension without precipitation of metal using a variety of acids. Although these methods help prepare a uniform suspension, the acids are rapidly decomposed during the calcining process, thereby worsening physical properties and performance of the catalyst.

To summarize, the conventional methods of preparing complex metal oxide catalysts tried to prevent phase separation and reduce suspension particle size in preparing precursor suspensions using an organic acid. While the problems of phase separation and particle size could be solved with the organic acid, the organic acid tends to be decomposed rapidly during the drying or calcining process, so that the surface area and physical properties of the catalyst are negatively affected.

DISCLOSURE

Technical Problem

As aforementioned, there have been a variety of researches on methods of preparing acrylic acid and methacrylic acid in good yield using the commonly used molybdenum-bismuth-cobalt-iron oxide catalyst and various complex oxide catalysts. However, a sustained development of oxide catalyst preparation methods is required to improve activity and selectivity of the catalyst.

Technical Solution

To order to solve the problems of the prior art, It is an object of the present invention to provide a catalyst for partial oxidation propylene or isobutylene, which can prevent rapid decomposition of an acid added to prepare the catalyst and thus maintain good selectivity for acrolein and methacrolein, show high activity for conversion of propylene and isobutylene and improve yield of acrylic acid and methacrylic acid by stabilizing the manufacturing process, and a preparation method thereof.

It is another object of the present invention to provide a method of preparing such unsaturated carboxylic acid as acrylic acid or methacrylic acid utilizing the catalyst for partial oxidation of propylene or isobutylene.

It is still another object of the present invention to provide a method of preparing unsaturated nitrile utilizing the catalyst for partial oxidation of propylene or isobutylene.

ADVANTAGEOUS EFFECTS

The present inventors completed the present invention by adding a drying control chemical additive, as a material capable of controlling decomposition of the organic acid which is commonly used to prepare a suspension, thereby maintaining the decomposition rate of the organic acid, fostering pore development of the catalyst and improving physical properties.

BEST MODE

In order to achieve these objects, the present invention provides a catalyst for partial oxidation having a surface area of 15-18 $m^2/g$, which is represented by the following Chemical Formula 1:

$$Mo_aBi_bFe_cX_dY_eO_f$$ [Chemical Formula 1]

Wherein

X is at least one element selected from the group consisting of Co and Ni;

Y is at least one element selected from the group consisting of K, Cs and Rb; and each of a, b, c, d, e and f represents the atomic mole ratio of each element, and when a is 12, b is 0.5~2, c is 0.5~2, d is 3~8, and e is 0.005~0.2, and f is determined according to the oxidation state of each metal.

The present invention also provides a method of preparing the catalyst represented by Chemical Formula 1, which comprises the steps of:

(a) dissolving an aqueous solution of at least one metal salt, the metal being selected from the group consisting of molybdenum, bismuth, iron, cobalt, nickel, potassium, cesium and rubidium in an organic acid and adding a drying control chemical additive to prepare a catalyst suspension;

(b) drying the catalyst suspension in vacuum and crushing it to obtain a catalyst powder; and (c) calcining the catalyst powder in air.

Most preferably, the catalyst represented by Chemical Formula 1 is used for partial oxidation of propylene or isobutylene.

The present invention further provides a method of preparing an unsaturated carboxylic acid comprising the step of partially oxidizing an alkane, an alkene or a mixture thereof in the presence of the complex metal oxide catalyst prepared according to the above methods.

The present invention further provides a method of preparing an unsaturated nitrile comprising the step of partially oxidizing an alkane, an alkene or a mixture thereof and ammonia in the presence of the metal oxide catalyst prepared according to the above methods.

MODE FOR INVENTION

Hereunder is given a more detailed description of the present invention.

The present invention is characterized by a catalyst having a good selectivity for acrolein and methacrolein, offering good activity for conversion of propylene and isobutylene and enabling stable manufacture operation.

The active component of the metal oxide catalyst is represented by Chemical Formula 1. The final catalyst prepared by using the drying control chemical additive has a surface area of 15-18 $m^2/g$, and thus has significantly improved catalytic activity. If the surface area is below 15 $m^2/g$, catalyst activity may decrease. Otherwise, if the surface area exceeds 18 $m^2/g$, the content of the drying control chemical additive such as propionic acid may increase and selectivity of acrolein may decrease.

Thus, the catalyst of the present invention is useful in preparing an unsaturated carboxylic acid through partial oxidation of an alkane, an alkene or a mixture thereof with oxygen. To take a preferred example, propylene or isobutylene may be reacted with oxygen in the presence of the catalyst represented by Chemical Formula 1 to obtain such unsaturated aldehyde as acrolein or methacrolein. The obtained acrolein or methacrolein may be oxidized further to obtain acrylic acid or methacrylic acid in high yield.

The method of preparing the complex metal oxide catalyst represented by Chemical Formula 1, or the catalyst for partial oxidation of the present invention, is described more specifically.

First, each metal salt of a complex metal oxide is dissolved using water and an organic acid. Then, a drying control chemical additive is added to prepare a catalyst suspension.

Next, the catalyst suspension is dried in vacuum to obtain a cake-shaped catalyst, which is crushed to obtain a catalyst in the powder form.

Lastly, the catalyst in the powder form is collected and calcined in a calcining furnace to obtain the complex metal oxide catalyst represented by Chemical Formula 1. The calcining condition is not particularly limited. For example, it can be performed in air. Preferably, the catalyst is calcined at 400-450° C. for 5-10 hrs.

The organic acid, which is used in preparing the precursor solution of the complex metal oxide catalyst, reacts with metal oxide to give a chelate compound. Because the chelate compound is soluble in water, it can prevent precipitation of metal during the manufacturing process and can reduce particle size of the catalyst. Another advantage of adding the organic acid is that as the organic acid is decomposed, pore formation on the metal oxide catalyst is facilitated, so that the surface area of the catalyst increases and the increased surface area improves catalytic activity. However, because the organic acid and water are decomposed rapidly during heat treatment process such as drying and calcining, part of the pores are damaged. Damage done to the pores reduces performance and surface area of the catalyst.

The present invention is characterized in adding a material having a surface tension smaller than that of water and a boiling point higher than that of water as drying control chemical additive in order to prevent rapid decomposition of the organic acid and water.

The drying control chemical additive may be at least one selected from the group consisting of glycerol, propionic acid, formamide, nitromethane, propyl alcohol, butyl alcohol, ethanediol, nitroethane, amyl acetate, ethyl propionate, ethyl malonate, furfurol, $(\alpha,\beta,\gamma)$-picoline, piperidine, phenylhydrazine, 1-pentanol, 3-methylbutanol and isovaleric acid. Preferably, it is formamide, propionic acid or glycerol.

The content of the drying control chemical additive is preferably 10-60 wt %, more preferably 20-40 wt %, per 100 wt % of the organic acid.

The precursor solution of the complex metal oxide catalyst of the present invention may be prepared by mixing an adequate amount of metal salt, suitable for preparing the complex metal oxide catalyst, with at least one solvent. The precursor solution may be a slurry, a dispersion, a solution or a combination thereof. Atomic proportion of each metal constituent present in the slurry, dispersion or solution should be equal to the metallic proportion of the complex metal oxide catalyst to be prepared.

Water is used as the solvent for preparing the precursor solution. Preferably, the amount of water is large enough to minimize or prevent phase separation and/or separation of each constituent during preparation and keep each constituent practically included in the solution. Accordingly, the amount of water may vary depending on the amount of the constituents and their solubility. If the amount of water is small, a slurry may be formed. But, preferably, the amount of water is large enough to easily form an aqueous solution during mixing.

The metal constituent of the complex metal oxide catalyst of the present invention may be in the form selected from the group consisting of an ammonium salt, nitrate, oxide, carbonate, chloride, sulfate, hydroxide and organic acid salt, but is not limited to them. The metal constituent may be at least one selected from the group consisting of molybdenum, bismuth, iron, cobalt, nickel, potassium, cesium and rubidium.

Preferably, the organic acid, which is added to prepare the catalyst suspension, is at least one organic acid having 1 to 10 carbon atoms selected from the group consisting of nitric acid, citric acid, maleic acid and oxalic acid. The content of the organic acid may be controlled depending on the total moles of the nitrate ions of the metal salt. Preferably, the organic acid is comprised in 0.5-10 moles per 1 mole of the nitrate ion of the metal salt.

The resultant catalyst is shaped into regular size and shape by such conventional method as extrusion. The reaction condition for preparing the catalyst is not particularly limited.

The catalyst represented by Chemical Formula 1 may be used as catalyst for partial oxidation to prepare an unsaturated carboxylic acid and an unsaturated nitrile.

The present invention provides a method of preparing an unsaturated carboxylic acid comprising the step of partially oxidizing an alkane, an alkene or a mixture thereof in the presence of the complex metal oxide catalyst prepared by the aforementioned method.

The present invention also provides a method of preparing an unsaturated nitrile comprising the step of partially oxidizing an alkane, an alkene or a mixture thereof and ammonia in the presence of the complex metal oxide catalyst prepared by the aforementioned method.

Preferably, in the preparation of the unsaturated carboxylic acid, acrylic acid or methacrylic acid is obtained from partial oxidation of propylene or isobutylene.

The catalyst may be utilized in preparation of acrolein and acrylic acid or methacrolein and methacrylic acid, for example, by catalytic oxidation of propylene in the vapor phase in a fixed-bed reactor. The reaction condition is not particularly limited.

Hereinafter, the present invention is described in more detail through examples. However, the following examples are only for the understanding of the present invention and they do not limit the present invention.

EXAMPLES

Preparation of Catalyst

Example 1

400 mL of distilled water was put in a 500 cc glass reactor and heated to 75° C. while stirring. 100 g of citric acid was dissolved and then 100 g of ammonium molybdate, 19.7 g of ferric nitrate and 54.95 g of cobalt nitrate were added, in that order, and dissolved completely. The solution was cooled to 50° C. and 34.35 g of bismuth nitrate and 0.286 g of potassium nitrate dissolved in nitric acid were added. Finally, 60 g of formamide was added to obtain a slurry solution. The slurry solution was dried in a 120° C. vacuum rotary dryer. The dried catalyst cake was collected and crushed to a size of 40 mesh to obtain a catalyst powder. The catalyst powder was collected and calcined in a calcining furnace of 450° C. for 5 hours to obtain a catalyst. The calcining process was performed in air. The resultant catalyst had a composition of $Mo_{12}Bi_{1.5}Co_{4.4}Fe_2K_{0.06}$.

Comparative Example 1

300 mL of distilled water was put in a glass reactor and heated to 75° C. 100 g of ammonium molybdate was dissolved and then 19.7 g of ferric nitrate, 60.44 g of cobalt nitrate, 34.35 g of bismuth nitrate and 0.286 g of potassium nitrate dissolved in nitric acid were added to the solution containing the molybdate. A catalyst was deposited. The catalyst was dried in a vacuum dryer. The dried cake was collected and crushed to a size of 40 mesh to obtain a catalyst powder.

The catalyst powder was treated in a calcining furnace of 450° C. for 5 hours. The resultant catalyst had a composition of $Mo_{12}Bi_{1.5}Cu_{4.4}Fe_2K_{0.06}$.

Comparative Example 2

400 mL of distilled water was put in a 500 cc glass reactor and heated to 75° C. while stirring. 100 g of citric acid was dissolved and then 100 g of ammonium molybdate, 39.4 g of ferric nitrate and 60.44 g of cobalt nitrate were added, in that order, and dissolved completely. The solution was cooled to 50° C. and 34.35 g of bismuth nitrate and 0.286 g of potassium nitrate dissolved in nitric acid were added to obtain a slurry solution. The slurry solution was dried in a 120° C. vacuum rotary dryer. The dried catalyst cake was collected and crushed to a size of 40 mesh to obtain a catalyst powder. The catalyst powder was collected and baked in a baking furnace of 450° C. for 5 hours to obtain a catalyst. The baking was performed in air. The resultant catalyst had a composition of $Mo_{12}Bi_{1.5}Co_{4.4}Fe_2K_{0.06}$.

Example 2

400 mL of distilled water was put in a 500 cc glass reactor and heated to 75° C. while stirring. 100 g of citric acid was dissolved and then 100 g of ammonium molybdate, 39.4 g of ferric nitrate and 60.44 g of cobalt nitrate were added, in that order, and dissolved completely. The solution was cooled to 50° C. and 34.35 g of bismuth nitrate and 0.286 g of potassium nitrate dissolved in nitric acid were added. Finally, 50 g of glycerol was added to obtain a slurry solution. Drying and calcining were performed in the same manner of Example 1. The resultant catalyst had a composition of $Mo_{12}Bi_{1.5}Cu_{4.4}Fe_2K_{0.06}$.

Example 3

400 mL of distilled water was put in a 500 cc glass reactor and heated to 75° C. while stirring. 100 g of citric acid was dissolved and then 100 g of ammonium molybdate, 19.7 g of ferric nitrate and 54.95 g of cobalt nitrate were added, in that order, and dissolved completely. The solution was cooled to 50° C. and 34.35 g of bismuth nitrate and 0.286 g of potassium nitrate dissolved in nitric acid were added. Finally, 20 g of propionic acid was added to obtain a slurry solution. Drying and calcining were performed in the same manner of Example 1. The resultant catalyst had a composition of $Mo_{12}Bi_{1.5}Cu_{4.4}Fe_2K_{0.06}$.

Example 4

A catalyst was prepared in the same manner of Example 3, except for using 40 g of propionic acid.

Example 5

A catalyst was prepared in the same manner of Example 3, except for using 60 g of propionic acid.

Comparative Example 3

A catalyst was prepared in the same manner of Example 3, except for using 80 g of propionic acid and 200 g of citric acid.

Experiment

Catalytic Activity Test

It is reported that, according to the conventional methods, conversion ratio of propylene is 90% or higher, selectivity for acrolein and acrylic acid is 85-98% and yield of acrolein and acrylic acid is 77-98%. However, it is meaningless to compare such values directly because the conditions for catalytic activity test may vary a lot.

To measure catalytic activity of the catalyst of the present invention, each prepared catalyst was manufactured into a pellet having a regular shape. The pellet was filled in a reactor to oxidize propylene into acrolein and acrylic acid. Reaction was performed at 200-350° C. and under a pressure of 1-3 atm. A reactant gas comprising 1-10 vol % of propylene, 1-15 vol % of oxygen, 5-60 vol % of water vapor and 20-80% of inert gas was introduced on the catalyst with a space velocity of 500-5000 hr (STP). The test result for Examples and Comparative Examples are given in Table 1 below. Conversion ratio of propylene and yield of acrolein were calculated according to Equations 1-3 below.

Conversion ratio of propylene(%)=[(Moles of reacted propylene)/(Moles of supplied propylene)]×100   [Equation 1]

Selectivity of acrolein(%)=[(Moles of produced acrolein)/(Moles of reacted propylene)]×100   [Equation 2]

Yield(%)=[(Moles of obtained acrolein and acrylic acid)/(Moles of supplied propylene)]×100   [Equation 3]

The invention claimed is:

1. A catalyst for partial oxidation having a surface area of 15-18 m²/g, which is represented by the following Chemical Formula 1:

[Chemical Formula 1]

$$Mo_aBi_bFe_cX_dY_eO_f \qquad (1)$$

wherein

X is at least one element selected from the group consisting of Co and Ni;

Y is at least one element selected from the group consisting of K, Cs and Rb;

each of a, b, c, d, e and f represents the atomic mole ratio of each metal, and when a is 12, b is 0.5~2, c is 0.5~2, d is 3~8, and e is 0.005~0.2, and f is determined according to oxidation state of each metal.

2. A method of preparing a catalyst for partial oxidation represented by the following Chemical Formula 1, which comprises the steps of:

(a) dissolving an aqueous solution of at least one metal salt, the metal being selected from the group consisting of molybdenum, bismuth, iron, cobalt, nickel, potassium, cesium and rubidium in an organic acid and adding a drying control chemical additive to prepare a catalyst suspension;

(b) drying the catalyst suspension in vacuum and crushing it to obtain a catalyst powder; and (c) calcining the catalyst powder in air

| | Drying control additive | | Reaction temperature (° C.) | Conversion ratio of propylene (%) | Selectivity of acrolein (%) | Yield of acrolein + acrylic acid (%) | Surface area (m²/g) |
|---|---|---|---|---|---|---|---|
| Example 1 | Formamide | Mo12Bi1.5Co4.4Fe2K0.06 | 320 | 98.5 | 87.73 | 89.05 | 15.7 |
| Example 2 | Glycerol | Mo12Bi1.5Co4.4Fe2K0.06 | 320 | 98.3 | 87.62 | 89.12 | 15.3 |
| Example 3 | Propionic acid | Mo12Bi1.5Co4.4Fe2K0.06 | 320 | 98.7 | 88.96 | 90.14 | 15.5 |
| Example 4 | Propionic acid | $Mo_{12}Bi_{1.5}Co_{4.4}Fe_2K_{0.06}$ | 320 | 99.1 | 90.37 | 91.2 | 17.7 |
| Example 5 | Propionic acid | $Mo_{12}Bi_{1.5}Co_{4.4}Fe_2K_{0.06}$ | 320 | 98.8 | 89.34 | 90.43 | 17.2 |
| Comp. Example 1 | — | $Mo_{12}Bi_{1.5}Co_{4.4}Fe_2K_{0.06}$ | 320 | 96.2 | 83.82 | 86.23 | 5.5 |
| Comp. Example 2 | Citric acid only | $Mo_{12}Bi_{1.5}Co_{4.4}Fe_2K_{0.06}$ | 320 | 97.3 | 84.88 | 87.23 | 12.3 |
| Comp. Example 3 | Propionic acid | $Mo_{12}Bi_{1.5}Co_{4.4}Fe_2K_{0.06}$ | 320 | 99.3 | 84.06 | 85.2 | 23.2 |

As seen in Table 1, the catalysts of the present invention (Examples 1-5) have superior conversion ratio of propylene, selectivity of acrolein and yield of acrolein and acrylic acid compared with those of Comparative Examples 1 to 3 because the drying control chemical additive prevents rapid decomposition of the organic acid, and thereby preventing damage of pores.

INDUSTRIAL APPLICABILITY

As apparent from the above description, the present invention offers a catalyst having good selectivity for such unsaturated aldehyde as acrolein or methacrolein, such unsaturated carboxylic acid as acrylic acid or methacrylic acid and unsaturated nitrile, offering good yield and enabling stable plant operation by using a drying control chemical additive to prepare the catalyst.

[Chemical Formula 1]

$$Mo_aBi_bFe_cX_dY_eO_f \qquad (1)$$

wherein

X is at least one element selected from the group consisting of Co and Ni;

Y is at least one element selected from the group consisting of K, Cs and Rb;

each of a, b, c, d, e and f represents the atomic mole ratio of each metal, and when a is 12, b is 0.5~2, c is 0.5~2, d is 3~8, and e is 0.005~0.2, and f is determined according to oxidation state of each metal.

3. The method of claim 2, wherein the drying control chemical additive is a material having a surface tension smaller than that of water and a boiling point higher than that of water.

4. The method of claim 2, wherein the drying control chemical additive is at least one selected from the group consisting of glycerol, propionic acid, formamide, nitromethane, propyl alcohol, butyl alcohol, ethanediol, nitroethane, amyl acetate, ethyl propionate, ethyl malonate, furfurol, (α,β,γ)-picoline, piperidine, phenylhydrazine, 1-pentanol, 3-methylbutanol and isovaleric acid.

5. The method of claim 2, wherein the drying control chemical additive is added in 10-60 wt % per 100 wt % of the organic acid.

6. The method of claim 2, wherein the organic acid is at least one organic acid having 1 to 10 carbon atoms, which selected is selected from the group consisting of nitric acid, citric acid, maleic acid and oxalic acid.

7. A method of preparing an unsaturated carboxylic acid comprising the step of partially oxidizing an alkane, an alkene or a mixture thereof in the presence of a catalyst represented by the following Chemical Formula 1, which has been prepared by the method of claim 2:

[Chemical Formula 1]

$$Mo_a Bi_b Fe_c X_d Y_e O_f \qquad (1)$$

wherein

X is at least one element selected from the group consisting of Co and Ni;

Y is at least one element selected from the group consisting of K, Cs and Rb;

each of a, b, c, d, e and f represents the atomic mole ratio of each metal, and when a is 12, b is 0.5~2, c is 0.5~2, d is 3~8, and e is 0.005~0.2, and f is determined according to oxidation state of each metal.

8. The method of claim 7, wherein the unsaturated carboxylic acid is acrylic acid or methacrylic acid.

9. A method of preparing an unsaturated nitrile comprising the step of partially oxidizing an alkane, an alkene or a mixture thereof and ammonia in the presence of a catalyst represented by the following Chemical Formula 1, which has been prepared by the method of claim 2:

[Chemical Formula 1]

$$Mo_a Bi_b Fe_c X_d Y_e O_f \qquad (1)$$

wherein

X is at least one element selected from the group consisting of Co and Ni;

Y is at least one element selected from the group consisting of K, Cs and Rb;

each of a, b, c, d, e and f represents the atomic mole ratio of each metal, and when a is 12, b is 0.5~2, c is 0.5~2, d is 3~8, and e is 0.005~0.2, and f is determined according to oxidation state of each metal.

* * * * *